(12) United States Patent
Powers

(10) Patent No.: US 9,415,230 B2
(45) Date of Patent: Aug. 16, 2016

(54) ENERGY EFFICIENT DEFIBRILLATION CURRENT LIMITER

(75) Inventor: Daniel Powers, Issaquah, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2415 days.

(21) Appl. No.: 12/161,809

(22) PCT Filed: Jan. 29, 2007

(86) PCT No.: PCT/IB2007/050295
§ 371 (c)(1),
(2), (4) Date: Jul. 23, 2008

(87) PCT Pub. No.: WO2007/088507
PCT Pub. Date: Aug. 9, 2007

(65) Prior Publication Data
US 2010/0228305 A1 Sep. 9, 2010

Related U.S. Application Data

(60) Provisional application No. 60/764,425, filed on Feb. 1, 2006.

(51) Int. Cl.
A61N 1/39 (2006.01)

(52) U.S. Cl.
CPC ............ *A61N 1/3906* (2013.01); *A61N 1/3931* (2013.01); *A61N 1/3912* (2013.01); *A61N 1/3937* (2013.01)

(58) Field of Classification Search
CPC . A61N 1/3906; A61N 1/3912; A61N 1/3925; A61N 1/3931; A61N 1/3937
USPC .......................................................... 607/5–6
See application file for complete search history.

(56) References Cited

U.S. PATENT DOCUMENTS

| 4,745,923 | A | | 5/1988 | Winstrom | |
|---|---|---|---|---|---|
| 5,275,157 | A | * | 1/1994 | Morgan et al. | 607/6 |
| 5,391,186 | A | * | 2/1995 | Kroll et al. | 607/5 |
| 5,431,688 | A | | 7/1995 | Freeman | |
| 5,433,732 | A | | 7/1995 | Hirschberg et al. | |
| 5,735,879 | A | | 4/1998 | Gliner et al. | |
| 6,041,254 | A | | 3/2000 | Sullivan et al. | |
| 6,047,212 | A | | 4/2000 | Gliner et al. | |
| 6,161,040 | A | * | 12/2000 | Blunsden | 607/5 |
| 6,230,054 | B1 | | 5/2001 | Powers | |
| 6,405,081 | B1 | * | 6/2002 | Lyster et al. | 607/5 |
| 6,539,258 | B1 | | 3/2003 | Sullivan et al. | |
| 6,745,073 | B1 | * | 6/2004 | Kroll | 607/7 |
| 2005/0101999 | A1 | | 5/2005 | Lyster et al. | |

FOREIGN PATENT DOCUMENTS

EP 1535645 A1 6/2005

OTHER PUBLICATIONS

MeanValueTheorem.*

* cited by examiner

Primary Examiner — Tammie K Heller

(57) ABSTRACT

A current limiter for a defibrillation pulse is powered by the defibrillation pulse and switches the current delivery path open and closed when an excessive current condition exists. The excessive current condition is sensed by a sense resistor of the current limiter. The controlled current is delivered by an inductor which delivers a current which varies in a range about a predetermined current level during excessive current conditions. The current limiter dissipates little energy of the defibrillation pulse so that most of the energy produced by the defibrillator is delivered to the patient.

18 Claims, 5 Drawing Sheets

ENERGY EFFICIENT DEFIBRILLATION CURRENT LIMITER

This invention relates to defibrillators for the resuscitation of patients experiencing cardiac arrest and, in particular, to a circuit which prevents the delivery of excessive defibrillation currents to the patient.

Automatic external defibrillators ("AEDs") deliver a high-voltage impulse to the heart in order to restore normal rhythm and contractile function in patients who are experiencing arrhythmia, such as ventricular fibrillation ("VF") or ventricular tachycardia ("VT"). There are several classes of defibrillators, including manual defibrillators, implantable defibrillators, and automatic external defibrillators. AEDs differ from manual defibrillators in that AEDs they are pre-programmed to automatically analyze the electrocardiogram ("ECG") rhythm to determine if defibrillation is necessary and to provide administration measures such as shock sequences of the appropriate energy level followed or succeeded by periods when CPR is administered to the patient. AEDs are thus suitable for use by rescuers with no extensive medical training. Manual defibrillators are used by experienced EMTs who are capable of reading a patient's ECG waveform, determining whether a shock is appropriate, then setting up the defibrillator to deliver the proper shock sequence and energy level.

One of the most effective defibrillation shock waveforms currently in use is the biphasic waveform. Defibrillators which produce biphasic waveforms are described in U.S. Pat. No. 5,735,879 (Gliner et al.) and U.S. Pat. No. 6,047,212 (Gliner et al.) for instance. In the defibrillators described in these patents the delivery circuitry produces a biphasic waveform which is tailored to a patient's impedance, which is the impedance presented by the chest of the patient between the two defibrillator electrodes. As explained in these patents, there are a number of characteristics of the biphasic waveform which should be controlled for the delivery of a therapeutically effective shock waveform. Many of these characteristics are a function of patient impedance. Referring to FIG. 1 for example, a biphasic waveform 10 is illustrated. This waveform is controlled to exhibit a desired initial voltage $V_i$ which declines during the positive phase 12 of the waveform to a voltage level of $V_{\phi 1e}$. The positive phase 12 has a duration of $T_{\phi 1}$. The negative phase 14 of the waveform 10 has a starting negative voltage of $V_{\phi 2s}$ which declines to a final voltage level of $V_f$. The negative phase of the pulse has a duration of $T_{\phi 2}$. It is desirable to maintain several of these waveform parameters within predefined limits. For instance the positive phase 12 should have a duration $T_{\phi 1}$ which is not too short, and there should be a ratio of the first phase duration $T_{\phi 1}$ to the second phase duration $T_{\phi 2}$ which is within a pre-defined range. If a phase of the pulse is too short, it will be shorter than the cellular response time of the heart, the chronaxie time. The decline of the starting voltage level $V_i$ to the level $V_{\phi 1e}$ at the end of the first phase should not be too great, so that an appreciable amount of the delivered energy will remain for delivery during the second phase. There should also be a controlled relationship between the initial starting voltage level $V_i$ and the final pulse voltage level, $V_f$.

These parameters are affected by the patient impedance as illustrated in FIG. 2. If the pulse waveform is applied to a low impedance patient the energy will be delivered more rapidly than desired. For instance the energy of the shock can be delivered predominately during the first phase 12 for a low impedance patient, resulting in a steep decline of the waveform during the first phase as shown in FIG. 2. The voltage level $V_{\phi 1e}$ is very low at the end of the first phase 12, allowing very little energy to be delivered during the second phase 14. The duration of the second phase $T_{\phi 2}$ is thus very short as the drawing illustrates. The ratios of the voltage levels and durations are therefore outside of acceptable limits for a therapeutically effective pulse.

Another problem caused by a low patient impedance is high levels of current flow. The current flow initially, $I_i$, is very high as the energy rapidly flows through the chest of the low impedance patient. An excessive current level can provide injury to the patient. Thus it is desirable to prevent the delivery of these excessive current levels.

A simple solution to this problem is to use a current limiting impedance $R_{cl}$ in series with the patient impedance $R_{pat}$ of the low impedance patient. The defibrillator 1 would thus deliver a waveform with current flow limited by this series impedance. However this solution has several drawbacks. One is that a significant amount of energy can be dissipated through this impedance. For example, if the current limiting impedance $R_{cl}$ were 20 ohms and the patient impedance $R_{pat}$ were only 10 ohms, only one third of the delivered energy would be delivered to the patient's heart. The EMT could set the defibrillator to deliver a pulse of a specific energy level but only a portion of that energy would actually be delivered to the patient. Furthermore, this current limiting impedance would affect the delivery of pulses to all patients, dissipating energy intended for high impedance patients when the current limiting impedance $R_{cl}$ is not needed. Thus it is desirable that the excessive current problem be resolved in a way which does not dissipate energy intended for the patient and which does not affect the delivery of energy to patients who do not present the problem of excessive currents.

In accordance with the principles of the present invention, a current limiter for a defibrillation waveform is provided which limits the current for low impedance patients without dissipating a significant amount of the energy intended for the patient. The current limiter includes a switching circuit which is activated by excessive current conditions during delivery of a biphasic pulse and limits the peak current by switching the delivery of energy. For high impedance patients the current limiter is not activated and delivery of waveforms proceeds without any effect from the current limiter circuit.

IN THE DRAWINGS

Figure 4:
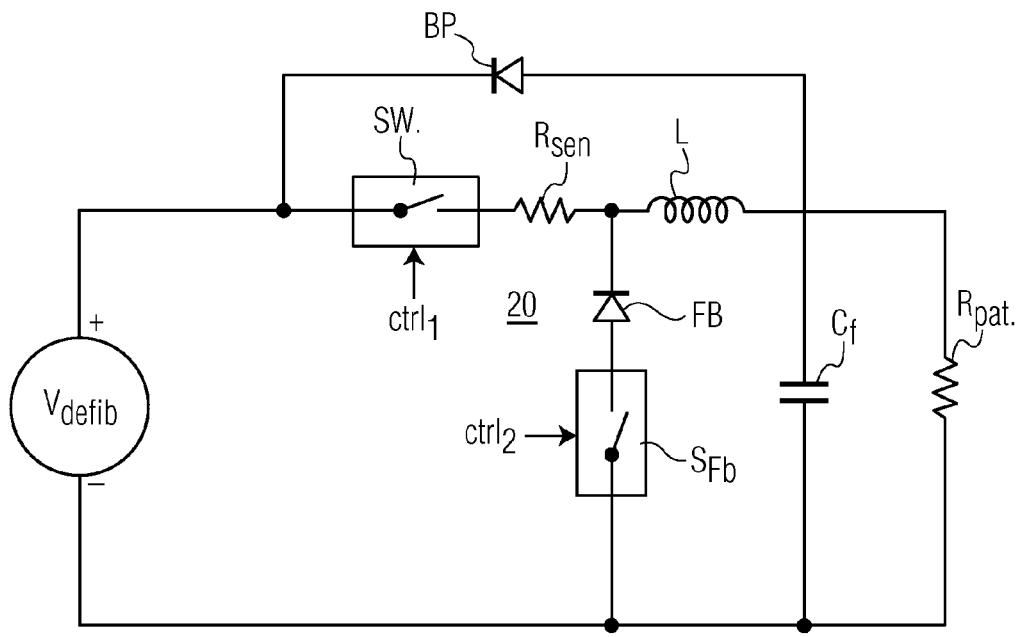
FIG. 4 illustrates a defibrillation current limiter constructed in accordance with the principles of the present invention.

Referring to FIG. 4, a current limiter 20 for a defibrillator constructed in accordance with the principles of the present invention is shown. In this example the current limiter 20 is intended to be easily adaptable to any existing defibrillator, requiring no special connections to the defibrillator or any other device. The current limiter in the example is thus fully contained external to the electrode connections of the defibrillator, represented by the defibrillator voltage $V_{defib}$, without any special connections for power or control signals. The current limiter 20 in this example connects to the existing defibrillator electrode lines and the circuit is entirely powered by the defibrillator pulse. In this example the current limiter circuit is coupled in series with one of the electrode lines, the "apex" line, which goes positive during the first phase of a biphasic shock waveform. The circuit is also coupled to the "sternum" line, the electrode line which goes negative during the second phase of the biphasic shock.

The apex electrode line, which goes positive relative to the sternum electrode line during the first phase 12 of a biphasic shock waveform, is coupled to a switch Sw. The switch Sw is controlled by a control signal $Ctrl_1$ which closes the switch Sw at the start of the first phase to deliver energy to the patient, represented by the patient impedance $R_{pat}$. The first phase of the biphasic pulse is delivered through a sense resistor $R_{sen}$ and an inductor L. The sense resistor $R_{sen}$ senses the flow of current being delivered to the patient and, when the current flow becomes excessive, the voltage drop across the sense resistor causes the switch Sw to open, interrupting the current flow. The energy stored by the magnetic field of the inductor L continues to source energy to the patient during this time, aided by energy stored by a filter capacitor $C_f$. The node between the sense resistor Rsen and the inductor L is prevented from becoming negative by a "free-wheeling" or flyback diode FB which, during the first phase of the biphasic waveform, is connected to the sternum line by closure of a flyback switch $S_{fb}$ during the first phase by a control signal $Ctrl_2$. The closure of the flyback switch also completes the loop circuit including the inductor L and the patient impedance $R_{pat}$. When the current flow drops to an acceptable level, as sensed by the sense resistor $R_{sen}$ the switch Sw closes again and defibrillator energy is again supplied from the defibrillator $V_{defib}$ to the patient $R_{pat}$ through the sense resistor $R_{sen}$, and the inductor L. This cycling on and off of the switch Sw continues about a nominal current limit $I_{nom}$, thereby effectively limiting peak defibrillator current to this level. Ripples in the delivered waveform are smoothed by the filter capacitor Cf. When enough energy has been delivered by the defibrillator such that the voltage produced has dropped below the level at which excessive currents are produced, the switch Sw remains closed, since excessive current is no longer sensed by the sense resistor $R_{sen}$. The first phase of the biphasic waveform times out as controlled by the defibrillator and the second, negative phase proceeds normally. During the second phase the current limiter circuit is not operating, as the series elements in the apex line are bypassed by the bypass diode BP which is forward-biased during the negative phase, and the flyback diode FB is disconnected from the sternum line by the opening of the switch $S_{fb}$ by the control signal $Crtl_2$.

Figure 5A:
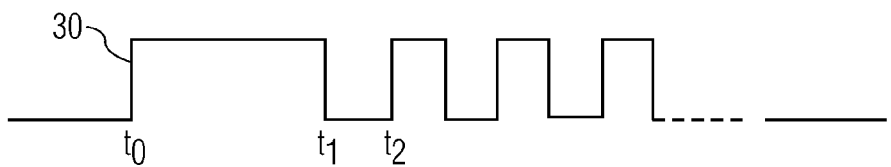
FIGS. 5a-5c illustrate waveforms used to explain the operation of the current limiter of FIG. 4.
Figure 5B:
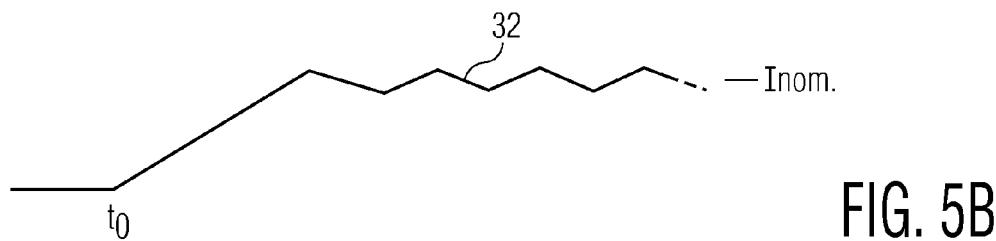
Figure 5C:
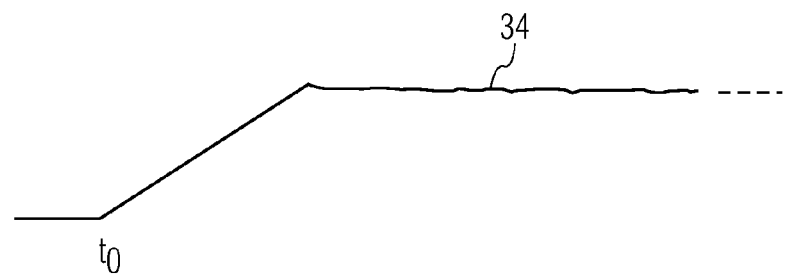

Waveforms illustrating this operation are shown in FIGS. 5a-5c. The waveform 30 of FIG. 5a illustrates the control signal $Ctrl_1$ which opens and closes switch Sw. At the start $t_0$ of the first phase 12 of a biphasic pulse waveform this control signal closes switch Sw as indicated by the positive-going signal 30 in FIG. 5a. During this time the current delivered by the defibrillator and the current limiter circuit 20 rises rapidly as shown by the current waveform 32 of FIG. 5b. The switch Sw will remain closed until such time as an excessive current level above the nominal current level $I_{nom}$ is sensed and the switch Sw opens, in this example, at time $t_1$. With the switch Sw open the current flow from the defibrillator stops and the current flow declines as shown by the declining current level between times $t_1$ and $t_2$. At time $t_2$ the current flow has declined below the level $I_{nom}$ and the control signal $ctrl_1$ closes the switch Sw again as by control signal 30. The switching of the switch Sw and the current flow continues in this manner until the current flow supplied by the defibrillator drops permanently below the level $I_{nom}$, at which time the switch Sw remains closed and biphasic waveform delivery continues without operation of the current limiter. During the period of current limiting the delivered waveform is smoothed by the filter capacitor as shown by waveform 34 of FIG. 5c.

Figure 6:
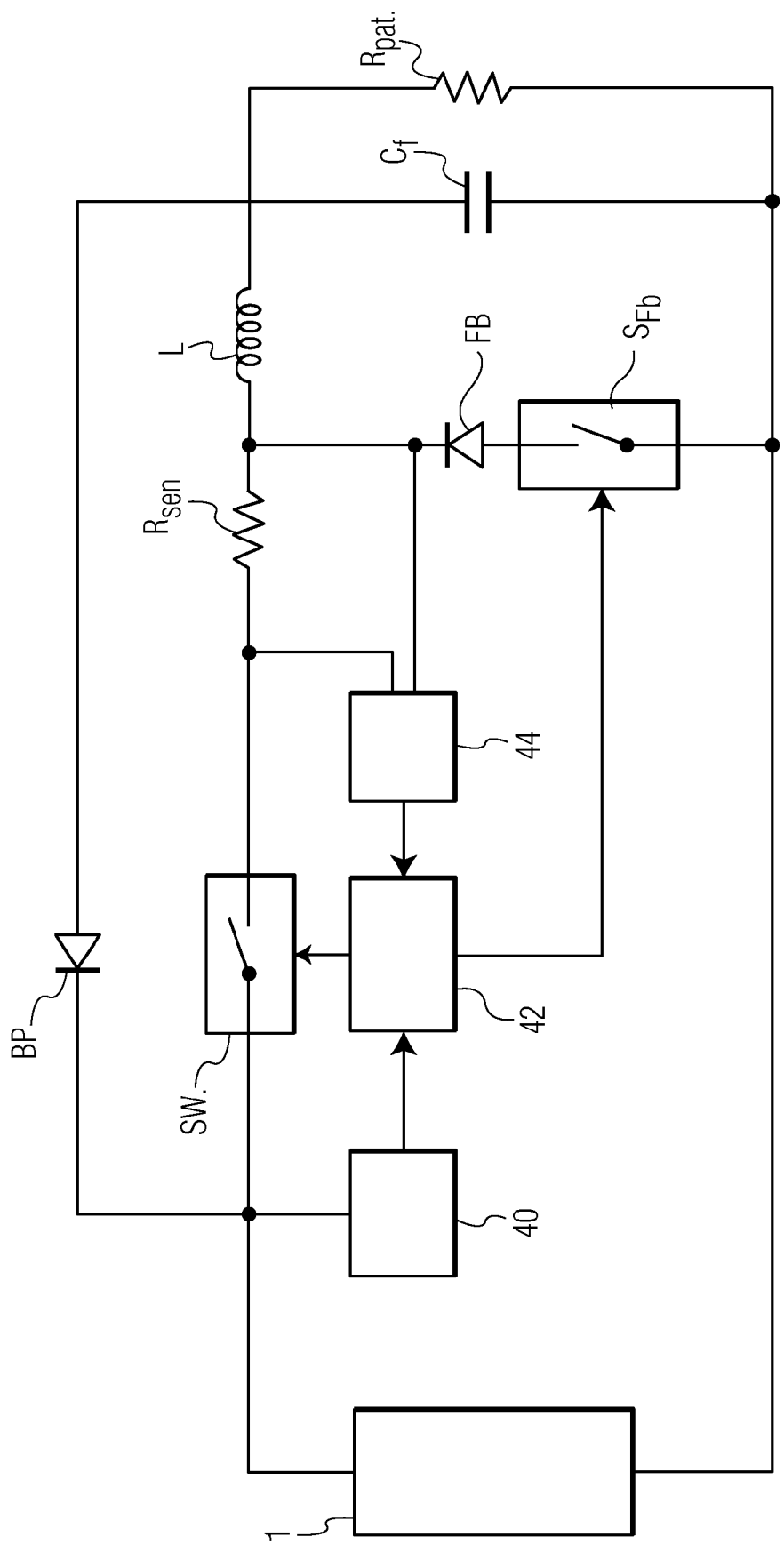
FIG. 6 is a second example of a current limiter constructed in accordance with the principles of the present invention.

FIG. 6 illustrates in block diagram form another example of a current limiter circuit of the present invention. This example is illustrated in circuit component detail in FIG. 7. The defibrillator 1 has the two conventional electrode leads marked as "apex" and "sternum". The apex lead in this example goes positive during the first phase of a biphasic pulse and is connected to the current limiter circuit at the input to a local power supply 40. The local power supply 40 is powered by the voltage of the positive-going first phase of a biphasic defibrillation pulse. During that time the local power supply 40 provides an energizing potential for the components of the current limiter. A control circuit 42 is powered by the local power supply 40 and receives another input from a sense circuit 44 and these two inputs result in the control signal used to open or close the switch Sw. The sense circuit 44 is coupled across the sense resistor $R_{sen}$ to sense the current being delivered to the inductor L and the patient represented by the patient impedance $R_{pat}$. When the current through the sense resistor $R_{sen}$ exceeds a threshold set by the sense circuit, its output signal causes the control circuit 42 to open the switch Sw, stopping the flow of current to the inductor L. This output signal also closes the switch $S_{fb}$ for the flyback diode so that the diode FB will complete the circuit including the inductor L and the patient impedance $R_{pat}$ as the inductive field continues to source current to the patient. The switching of the switch Sw continues in this manner until the current delivered falls below the threshold of the sense circuit for the balance of the positive-going portion of the biphasic pulse. During the negative phase the bypass diode BP bypasses the current limiter and the switch $S_{fb}$ disconnects the flyback diode FB from the sternum line.

Figure 7:
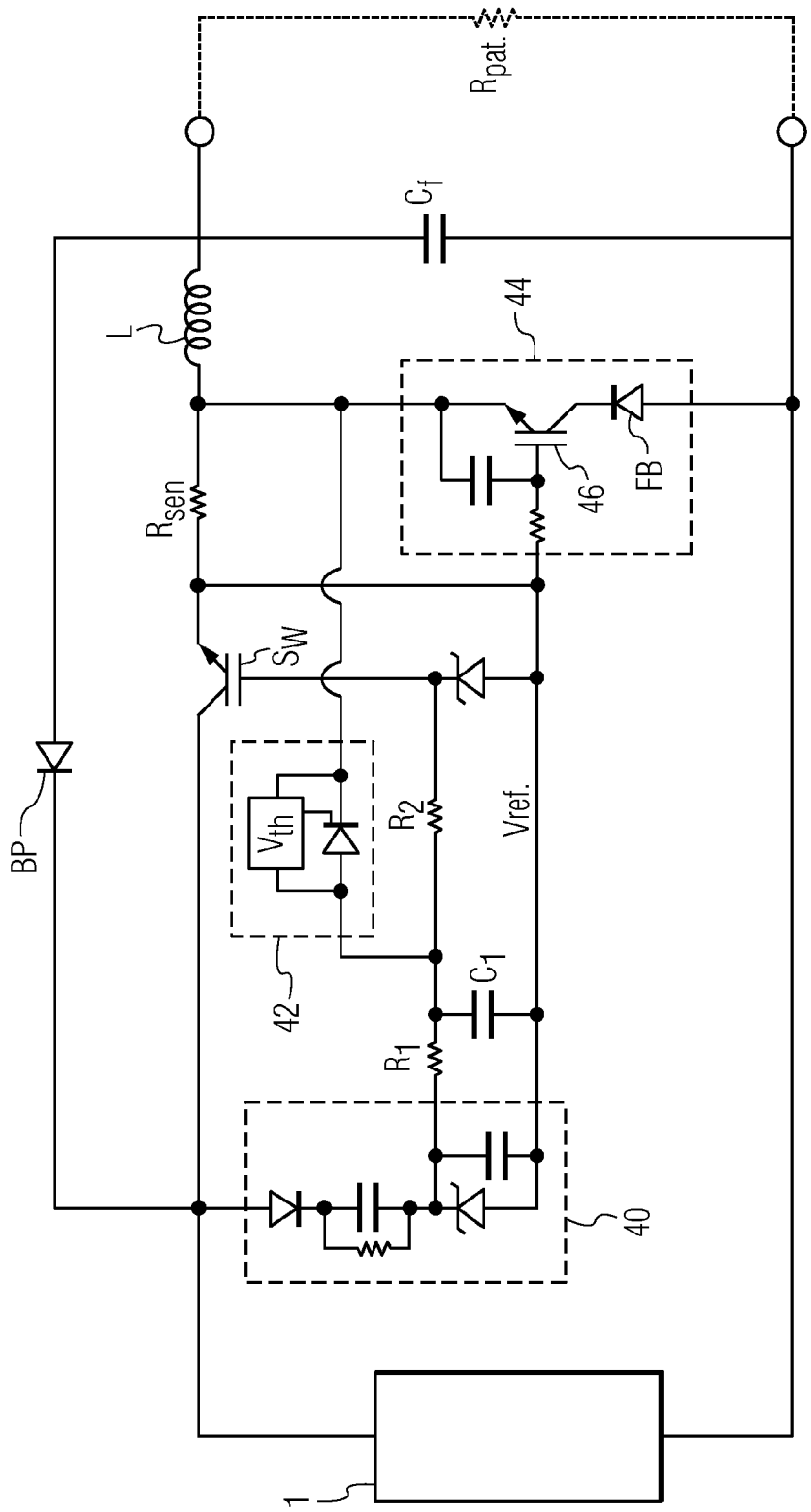
FIG. 7 is a detailed drawing of the current limiter circuit of FIG. 6.

In the component-level drawing of FIG. 7 it is seen that the local power supply 40 includes a zener diode which sets its regulated output voltage level. The output voltage of the local power supply is referenced to a local reference potential at the conductor marked $V_{ref}$. The local reference potential conductor is coupled to one side of the sense resistor $R_{sen}$. The output voltage of the local supply is applied by resistors $R_1$ and $R_2$ to the gate of the switch Sw which in this example is an IGBT solid-state switch. The voltage from the local power supply 40 causes the IGBT to become conductive, coupling energy from the defibrillator 1 to the patient by way of the sense resistor $R_{sen}$ and the inductor L. The resulting voltage drop across the sense resistor $R_{sen}$ is applied across the control circuit 44 for the flyback diode FB, which includes an IGBT 46, causing the IGBT to become conductive, coupling the flyback diode to the node between the sense resistor $R_{sen}$ and the inductor L. The local power supply voltage is also coupled to a SIDACTOR 42, the term used here to signify the shown voltage threshold $V_{th}$ applied to an SCR. SIDACTOR is a trademark registered by LITTELFUSE, INC., Chicago, Ill. The SIDACTOR remains nonconductive until such time as the voltage level from the local power supply and the voltage across the sense resistor $R_{sen}$ exceed a voltage threshold $V_{th}$ of the SIDACTOR 42. When this happens the SCR becomes conductive and clamps the output of the local power supply to the node between the sense resistor $R_{sen}$ and the inductor L. This clamping of the output of the local power supply to the node between the sense resistor $R_{sen}$ and the inductor L divert supply current away from the gate of the IGBT Sw and the IGBT Sw opens, disconnecting the supply of biphasic pulse current to the patient. The inductor L will continue to sustain current delivery to the patient at this time from the energy stored in its magnetic field. Thus, there will not be a sudden drop in the waveform delivered to the patient. Energy delivery is further aided at this time by energy stored by the filter capacitor $C_f$. This clamping by the SIDACTOR continues for so long as the "hold" current of the SCR is maintained, which is set by the value of resistor $R_1$. The flyback diode remains connected by the closure of the IGBT 46, which remains closed by the time constant of the resistor and capacitor of the control circuit 44. When the voltage across the sense resistor $R_{sen}$ declines such that the threshold of the SIDACTOR 42 is no longer exceeded and the hold current of the SCR is no longer met, the SIDACTOR clamp will open, the IGBT switch Sw can be closed again by the power supply 40, and the cycle continues.

The switching of the IGBT switch Sw continues in this manner until the voltage level of the applied defibrillation pulse drops to a level which is insufficient to switch the SCR clamp and render the IGBT nonconductive. The positive phase of the biphasic pulse then ends in the normal manner and the current limiter circuit is bypassed by the bypass diode BP during the negative phase of the biphasic pulse. The power supply 40 no longer biases the IGBR switch Sw closed during the negative-going phase of the biphasic pulse, and no voltage is developed across the sense resistor Rsen to maintain the IGBT 46 of the flyback circuit closed. Thus, the current limiter is inactive during the negative-going phase of the biphasic pulse. It is seen in this example that all of the current applied to the current limiter by the defibrillation pulse can only flow through the inductor L and to the patient. The regulator will switch in a narrow range of current levels around $I_{nom}$, resulting in very little of the applied defibrillation pulse energy being dissipated by the current limiter circuit.

Figure 1:
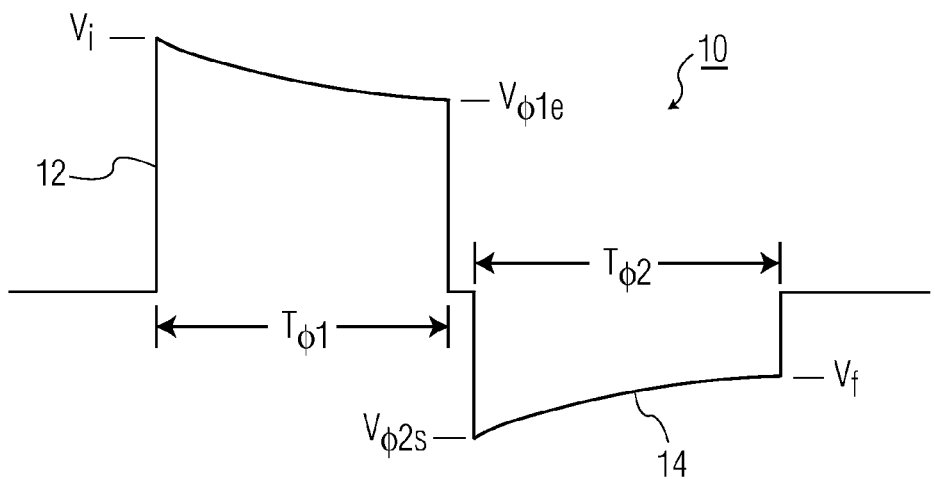
FIG. 1 illustrates a biphasic defibrillation waveform.
Figure 2:
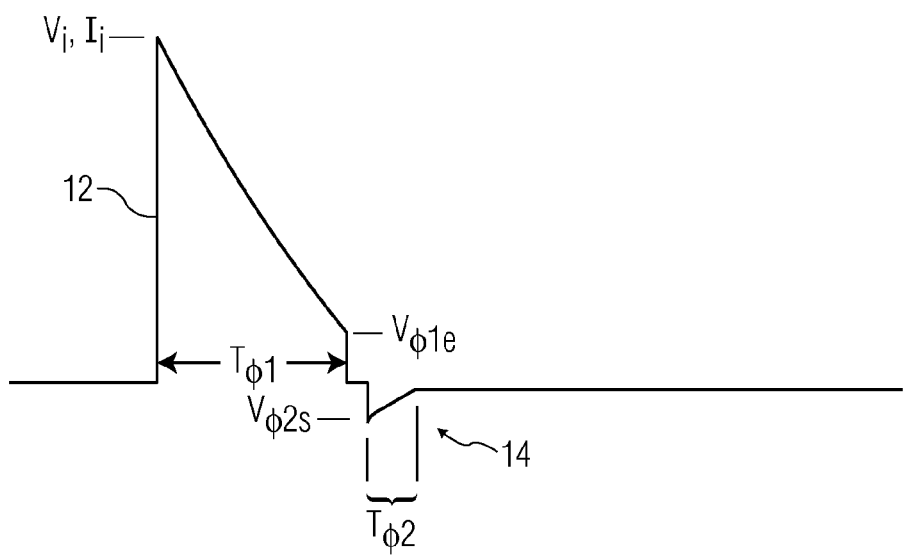
FIG. 2 illustrates a biphasic waveform delivered to a low impedance patient.
Figure 3:
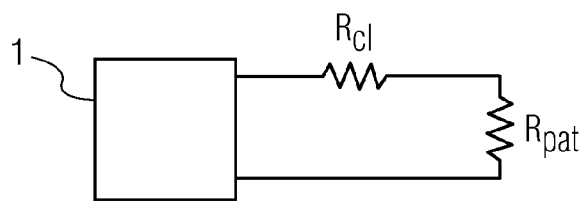
FIG. 3 illustrates a defibrillator with a current limiting impedance in series with the patient impedance.
Figure 8A:
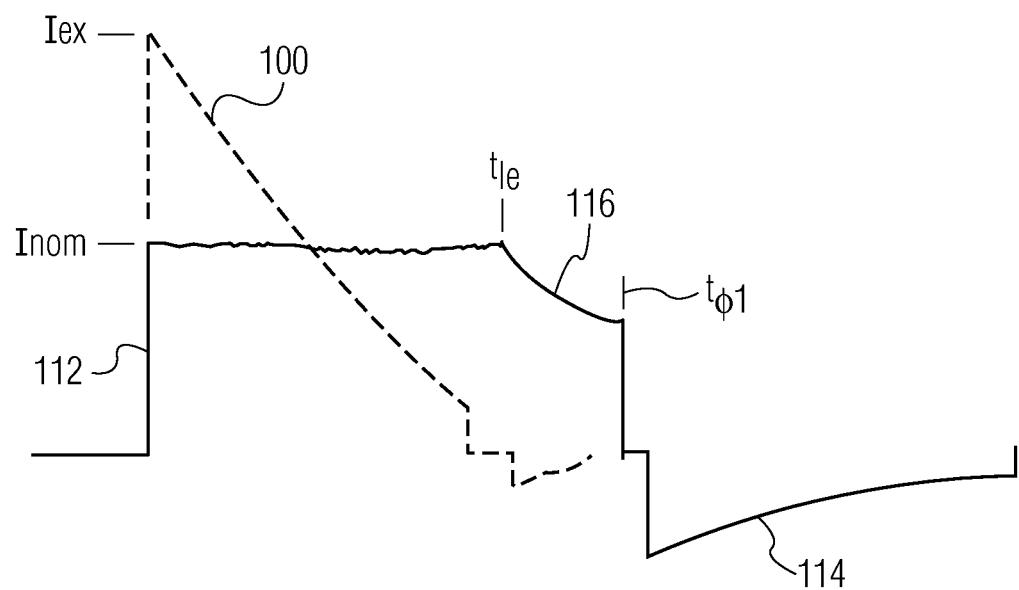
FIGS. 8a and 8b illustrate waveforms typical of a defibrillator of the present invention.
Figure 8B:
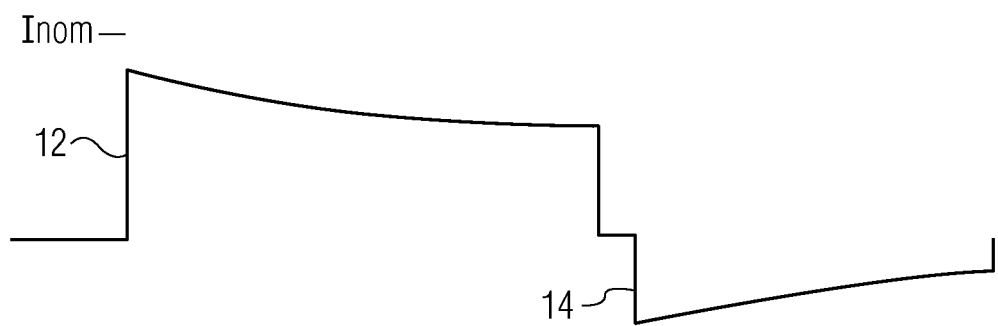

The effect of a defibrillation pulse current limiter of the present invention can be appreciated with reference to FIGS. 8a and 8b. Instead of a positive-going pulse which reaches an excessive current level $I_{ex}$ and rapidly declines as shown by the dashed line 100 in FIG. 8a (compare FIG. 2), the positive-going phase 112 of the biphasic pulse will rise until current level $I_{nom}$ is reached, at which time the pulse output current is limited about the $I_{nom}$ level. Current limiting continues until time $t_{1e}$ when current limiting ends as the output current of the pulse falls below the $I_{nom}$ level. The pulse 112 will then decline with the normal decay as shown by portion 116 of the pulse until the end of the first phase pulse at time $t_{\phi 1}$. At this termination level of the first phase pulse, a significant amount of energy remains to be delivered during the second phase 114 of the biphasic pulse.

FIG. 8b illustrates that a biphasic pulse applied to a high impedance patient will fail to reach the critical threshold $I_{nom}$ at which the current limiter begins to limit output current. The biphasic pulse 12, 14 of FIG. 8b is thus delivered in the normal fashion without any switching effect of the current limiter circuit.

A current limiter of the present invention may be used with either an AED or a manually operated defibrillator.

What is claimed is:

1. A current limiter for a defibrillation pulse produced by a defibrillator having first and second defibrillation pulse outputs designed to be coupled to patient electrodes comprising:
a switching circuit, a sense resistor, and an inductor coupled to the first defibrillation pulse output and a patient electrode;
a source of supply voltage coupled to the first defibrillation pulse output which supplies an operating potential for the switching circuit; and
a control circuit responsive to the potential across the sense resistor to switch the switching circuit during a condition of excessive current,
wherein the control circuit switches the switching circuit during an excessive current condition to prevent the delivery of excessive current to the patient electrode.

2. The current limiter of claim 1, wherein the switching circuit includes a solid-state switch which is switched open and closed during the condition of excessive current.

3. The current limiter of claim 2, wherein the solid-state switch comprises an IGBT device.

4. The current limiter of claim 1, wherein the switching circuit, the sense resistor, and the inductor are coupled in series between the first defibrillation pulse output and a patient electrode.

5. The current limiter of claim 4, wherein the first defibrillation pulse output is the positive-going output during delivery of the first phase of a biphasic pulse and the patient electrode comprises the apex patient electrode.

6. The current limiter of claim 1, wherein the control current acts to switch the switching circuit after a predetermined current limit is attained, and further acts to switch the output current produced by the current limiter about the predetermined current limit.

7. The current limiter of claim 6, further comprising a filter capacitor coupled to smooth the output pulse level produced during current limiting.

8. The current limiter of claim 1, wherein the inductor operates to source current when the switching circuit is switched to a nonconductive state.

9. The current limiter of claim 1, wherein the source of supply voltage is energized by a defibrillation pulse to supply an operating potential for the switching circuit.

10. The current limiter of claim 1, further comprising a bypass diode which is operative to bypass the current limiter during the negative-going phase of a biphasic defibrillation pulse.

11. The current limiter of claim 1, wherein the control circuit is only operative to switch the switching circuit during a positive-going phase of the biphasic defibrillation pulse.

12. A method for limiting the current delivered to a patient during delivery of a biphasic defibrillation pulse comprising:
applying a biphasic defibrillation pulse through a switching circuit;
causing the switching circuit to become nonconductive when the current delivered by the defibrillation pulse exceeds a predetermined limit;
causing the switching circuit to become conductive again when the current delivered by the defibrillation pulse falls below the predetermined limit; and
terminating the switching of the switching circuit when the current delivered by the defibrillation pulse remains below the predetermined limit.

13. The method of claim 12, wherein the switching circuit is energized by the energy of the defibrillation pulse.

14. The method of claim 12, wherein the switching circuit further includes a sense resistor,
wherein causing the switching circuit to become nonconductive is effected when the current through the sense resistor exceed a predetermined level.

15. The method of claim 14, wherein causing the switching circuit to become conductive again is effected when the current through the sense resistor falls below the predetermined level.

16. The method of claim 12, further comprising energizing the switching circuit with the energy of the applied biphasic defibrillation pulse.

17. The method of claim 12, further comprising actuating the switching circuit to become nonconductive and conductive again only during the positive-going phase of a biphasic defibrillation pulse.

18. The method of claim 17, further comprising bypassing the switching circuit during the negative-going phase of the biphasic defibrillation pulse.

* * * * *